United States Patent
Pariseau et al.

(10) Patent No.: US 9,677,990 B2
(45) Date of Patent: Jun. 13, 2017

(54) PARTICLE COUNTER WITH ADVANCED FEATURES

(71) Applicant: Particles Plus, Inc., Stoughton, MA (US)

(72) Inventors: David Pariseau, Los Altos, CA (US); Michael Hodel, Fremont, CA (US); Adam Giandomenico, Sharon, MA (US)

(73) Assignee: Particles Plus, Inc., Stoughton, MA (US)

( * ) Notice: Subject to any disclaimer, the term of this patent is extended or adjusted under 35 U.S.C. 154(b) by 0 days.

(21) Appl. No.: 14/701,485

(22) Filed: Apr. 30, 2015

(65) Prior Publication Data

US 2015/0316463 A1    Nov. 5, 2015

Related U.S. Application Data

(60) Provisional application No. 61/986,532, filed on Apr. 30, 2014.

(51) Int. Cl.
| | |
|---|---|
| *G01N 1/00* | (2006.01) |
| *G01N 15/02* | (2006.01) |
| *G01N 21/00* | (2006.01) |
| *G01N 33/50* | (2006.01) |
| *G01N 27/00* | (2006.01) |
| *G01N 15/14* | (2006.01) |

(52) U.S. Cl.
CPC ..... *G01N 15/1459* (2013.01); *G01N 15/1429* (2013.01); *G01N 2015/1486* (2013.01)

(58) Field of Classification Search
CPC ........... G01N 15/1429; G01N 15/1459; G01N 2015/1486; G01N 15/0205; G01N 15/14; G01N 2015/1006; G01N 15/12; G01N 15/1456; G01N 2015/0073; G01N 2015/0084; G01N 2015/1402; B01L 2200/0652
USPC ........ 356/337, 336, 39, 438; 702/21, 19, 66; 324/71.4

See application file for complete search history.

(56) References Cited

U.S. PATENT DOCUMENTS

| | | | |
|---|---|---|---|
| 7,439,855 B1 * | 10/2008 | Yufa | G01D 21/00 340/539.1 |
| 2008/0221812 A1 * | 9/2008 | Pittaro | G01N 15/14 702/66 |
| 2012/0012744 A1 * | 1/2012 | Wang | G01N 15/0205 250/287 |
| 2013/0040857 A1 * | 2/2013 | Anderson | G01N 33/6848 506/12 |
| 2013/0295588 A1 * | 11/2013 | Watkins | C12M 41/36 435/7.24 |

FOREIGN PATENT DOCUMENTS

WO    2012064878    *  5/2012 ............ C12M 41/36

* cited by examiner

*Primary Examiner* — Sunghee Y Gray (57) ABSTRACT

An airborne or liquid particle sensor with a number of advanced features is disclosed. The sensor includes an output channel generating an electrical signal for a particle passing through the sensor, where the electrical signal includes information related to the pulse. The information is processed by the sensor to determine a value that indicates a more accurate particle mass for a sample period than the average mass.

5 Claims, 3 Drawing Sheets

PARTICLE COUNTER WITH ADVANCED FEATURES

CROSS-REFERENCE TO RELATED APPLICATION

This application claims priority to U.S. Provisional Application Ser. No. 61/986,532 filed on Apr. 30, 2014, titled PARTICLE COUNTER WITH ADVANCED FEATURES by inventors David PARISEAU, et al., the entire disclosure of which is hereby incorporated herein by reference.

This application is related to and incorporates by reference: U.S. Non-Provisional application Ser. No. 14/214,899, filed herewith on Mar. 15, 2014, titled PARTICLE COUNTER WITH INTEGRATED BOOTLOADER by inventor David Pariseau; U.S. Non-Provisional application Ser. No. 14/214,870, filed herewith on Mar. 15, 2014, titled PERSONAL AIR QUALITY MONITORING SYSTEM by inventors David Pariseau and Adam Giandomenico; U.S. Non-Provisional application Ser. No. 14/214,903, filed herewith on Mar. 15, 2014, titled MIXED-MODE PHOTO-AMPLIFIER FOR PARTICLE COUNTER by inventors David Pariseau and Ivan Horban; U.S. Non-Provisional application Ser. No. 14/214,876, filed herewith on Mar. 15, 2014, titled MULTIPLE PARTICLE SENSORS IN A PARTICLE COUNTER by inventor David Pariseau; U.S. Non-Provisional application Ser. No. 14/214,889, filed herewith on Mar. 15, 2014, titled INTELLIGENT MODULES IN A PARTICLE COUNTER by inventor David Pariseau; U.S. Non-Provisional application Ser. No. 14/214,895, filed herewith on Mar. 15, 2014, titled PULSE SCOPE FOR PARTICLE COUNTER by inventor David Pariseau; and U.S. Non-Provisional application Ser. No. 14/214,907, filed herewith on Mar. 15, 2014, titled PULSE DISCRIMINATOR FOR PARTICLE COUNTER by inventors David Pariseau and Ivan Horban, the entire disclosures of which are hereby incorporated herein by reference.

BACKGROUND

Particle counters have been used for decades in manufacturing or industrial applications to measure particulate quantities in air, gases or liquids. Typically such counters also group particulates by size. These size channels vary by application and often by instrument. A particle counter has at least one size channel and popular counters can have 6 or more channels. Typically these size channels discriminate pulses based on the pulse height of the incoming signal, which is a measure of the light blocked or scattered as particles interrupt a light beam (typically a laser). These counts are then often displayed on a local display as differential counts (particles for a given size channel) or cumulative counts for this size channel and all larger channels. The counts are typically logged in some local memory and can also be communicated via some external interface to facility monitoring systems, or remote computers or devices.

SUMMARY

In accordance with the aspects of the invention, a system and a method are disclosed that enhance the functionality of traditional particle sensors or counters for airborne and liquid particles. The embodiments set forth, in accordance with the aspects of the invention, extend the functionality of traditional particle counters by adding advanced features and functions. These features and functions provide enhance functionality, which adds value to these instruments and allows them to provide both new information, and to process existing information in order to make it more useful and accessible to users. This adds significant value to standard instrumentation.

BRIEF DESCRIPTION OF THE DRAWINGS

The following detailed description is directed to certain sample embodiments. However, the disclosure can be embodied in a multitude of different ways as defined and covered by the claims. In this description, reference is made to the drawings wherein like parts are designated with like numerals throughout.

DETAILED DESCRIPTION

In accordance with the invention, it should be observed that the embodiments reside primarily in combinations of method step and apparatus components related to facilitating the invention. Accordingly the components and method steps have been represented where appropriate by conventional symbols in the drawing showing only those specific details that are pertinent to understanding the embodiments of the invention so as not to obscure the disclosure with details that will be readily apparent to those of ordinary skill in the art having the benefit of the description herein.

Unless defined otherwise, all terms used herein have the same meaning as commonly understood by one of ordinary skill in the art to which this invention belongs. Any methods and systems, similar or equivalent to those described herein, can also be used in the practice of the invention. Representative illustrative methods and embodiments of systems are also described in accordance with the aspects of the invention.

It is noted that, as used in this description, the singular forms "a," "an" and "the" include plural referents unless the context clearly dictates otherwise. Reference throughout this specification to "an aspect," "one aspect," "various aspects," "another aspect," "one embodiment," "an embodiment," "certain embodiment," or similar language means that a particular aspect, feature, structure, or characteristic described in connection with the embodiment is included in at least one embodiment of the invention. Thus, appearances of the phrases "in one embodiment," "in at least one embodiment," "in an embodiment," "in certain embodiments," and similar language throughout this specification may, but do not necessarily, all refer to the same embodiment.

Figure 1:
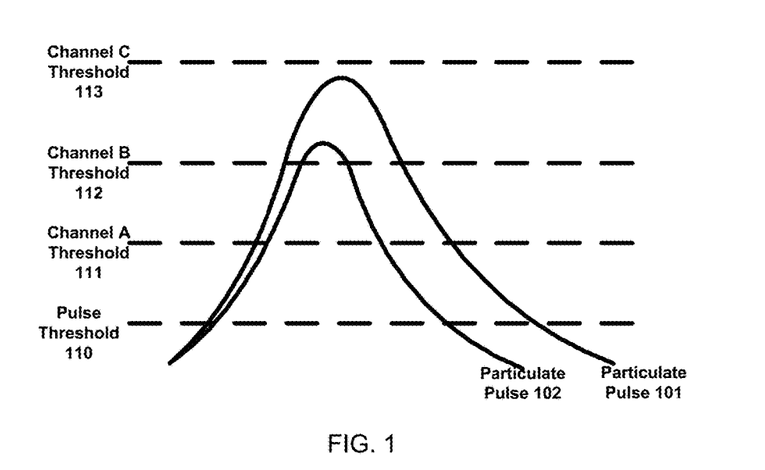
FIG. 1 illustrates a pulse output of a particle sensor in accordance with the various aspects of the invention.

Referring now to FIG. 1, in accordance with various aspects of the invention, an example of a pulse, which is an example of an output by a particle sensor (typically a photo-detector and amplifier) created by a particulate passing through a light beam (typically a created by a laser). The pulse depicts the voltage output of an amplifier over time, though it could be transmitted in a variety of other means (for example current pulse over time).

Pulses are typically qualified by some baseline threshold to allow for discrimination of valid pulses from noise. Valid pulses would then be, in accordance with some aspects of the invention, those signals above this baseline threshold. Once a pulse crosses such a threshold 110 it is sized by channel typically based on the peak amplitude of the pulse (though in some cases pulse-width might also be a factor, as in some discriminators designed by Particles Plus, Inc.). In the example in FIG. 1, the particulate pulses 101,102 would both be binned in an A channel 111 and a B channel 112, but would not be binned in a C channel 113, since the peak amplitude of these particulate pulses 101 and 102 does not cross the threshold for the C channel 113. In this example, the mass of particulates in the B channel 112 would include all particles with peaks between the B channel's 112 threshold and the C channel's 113 threshold. The amount of light scattered by the two pulses 10 and 102 are substantially different. For the purposes of this graphic, both pulses are shown overlaid on each other, but in reality they would be separated in time.

True Mass Calculation

Typically when estimating total particulate mass, particle counters take the number of counts in each size (herein size refers to a range) channel and then the counter calculates an average mass for the particles in this channel based on an average size estimated at the size of particles in the middle of that channel, for example if there was 0.3 um channel followed by a 0.5 um channel then the average size of the 0.3 um channel would be assumed to be 0.4 um (the middle of the 0.3 um or (0.5 um-0.3 um)/2+0.3 um. Of course other methods might be used to arrive at an estimated size, perhaps this parameter might even be made to be configurable, the key concept is that current generations of instruments attempt to attribute a single average size to all particulates in that channel for the purposes of calculating particle mass.

To estimate the mass of particles in that channel for a given sample the counter takes the average particle size (discussed above), converts that size to volume of material, multiplies this by the expected density of that material to arrive at the mass of an average particle for that channel and then multiplies it by the number of particles counted during a sample to arrive at the particle mass for that channel during that sample. That figure can then be used directly or scaled to some standard volume to infer what the particle mass for a standard volume of air of this particle size would be based on this representative sample, Multiple channels could be added together to give a sense of total-particle-mass for the instrument's entire range or some subset thereof, Theses masses are then displayed either as a mass per channel or the total mass for all the channels. Since no information on actual particle sizes is retained in the counter, the estimated average size of particles in a channel can lead to potentially large errors in estimated mass versus the actual mass, when the actual average size differs from the estimated average size.

To refine this estimate, one can factor in the index of refractivity, the density of particulates, even some assumed geometry for the particles. This helps to some extent, if data associated with these factors for the particulates being counted are available. However, it doesn't address the issue that particulates are all grouped in a single channel and an average of the mass of particles in that channel has to somehow choose a single value, which may also be represented in a range- to describe this population of particulates.

Typically when particulates are added to a particular channel's counter the detailed information on that particulate is lost. If however, the mass of the particulate is calculated during the acquisition of that particle and transmitted as an estimate of its actual mass to the channel manager, then the system can accumulate not only counts (occurrences of particles) but a sum of the estimated masses of each particulate as it arrived. This would provide a far more accurate measure of mass than averaging an entire channel could provide.

In accordance with some aspects of the invention, to derive a better estimate of mass, the system would integrate the area under a pulse curve for the duration of the pulse above the pulse threshold. By integrating that entire area, the system would have a more accurate measure of the actual light energy scattered by the particulate as the particles transited the beam. This would require many consecutive voltage measurements of the pulse, with each of these summed to provide an overall measurement of the area.

In accordance with various aspects of the invention, to derive an estimate of the mass, the system simply measures the pulse peak-height- and the pulse width (in accordance with one aspect, it would be done at the pulse threshold) and multiply the two to arrive at a 2D representation of the area. This may be less accurate. Thus, in accordance with some aspects of the invention, a correction factor is applied to this measurement to account for the expected shape of such a pulse. This, in accordance with various aspects of the invention, is based either on a theoretically calculated or an empirically derived formula. This would allow the system to quickly derive an estimated mass for each particle as it arrived. If these "areas" were summed and communicated along with the counts for each channel, then the system could arrive at a more accurate measure of total mass.

In accordance with aspects of the invention, the mass of the particles, in a given channel, is accumulated during the sample by calculating or estimating the actual size of each particle as it is processed with these values being summed together to provide a more accurate estimate of the total particle mass than is traditionally seen with an arithmetic average based on the total particles counted times an estimated average size.

Channel Synchronization

Errors often accrue in a counter when attempting to synchronize the accumulation of counts from various channels over time. A controller managing such is burdened with many other tasks. As such there are often latencies in channel management which can entail reading peak pulses voltages or reading external channel counters (in the case of wrapping of such counters these might require several reads). All of this typically occurs linearly and, as such, small timing errors can occur and accumulate that can sometimes skew certain results or values. These are typically small variations and are largely ignored.

However, if a system is implemented with a fast pulse-processing parallel front-end (for example, like with an FPGA) then many of these errors can be eliminated. The front-end can process each pulse in and manage the counters in parallel, and all of the data can be latched in a single operation (likely at the request of the main controller). In this way, when requested, the front-end can latch all of the counters simultaneously, as well as the accumulated mass (if available, as outline above), as well as the elapsed time since the last latch, etc. In that way all of the timing issues inherent in a single controller implementation are removed since the data arrives all synchronized and with an accurate elapsed time so that calculations based on these values will have increased accuracy.

Figure 2:
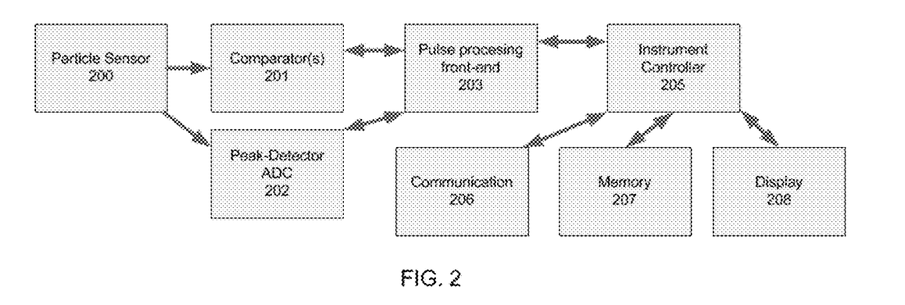
FIG. 2 is a particle counting system or instrument in accordance with the various aspects of the invention.

Referring now to FIG. 2, a system is represented in accordance with the aspects of the invention. The system includes a particle sensor 200. The particle sensor 200 converts incoming particulates to electrical pulses. A pulse processing front-end 203, which could easily be implemented in an FPGA (as described above) or even with discrete logic, a DSP, or a fast, dedicated controller, manages the processing of those pulses. The pulse processing front-end 203 would set at least one threshold for at least one comparator 201 and get an estimate of pulse width by recording the time for pulses above the threshold.

In accordance with other aspects and embodiments of the invention, a peak-detector and analog-to-digital converter 202 would be setup to measure an accurate peak height for each pulse, and combined with the pulse width for that pulse (based on the comparator 201 output) to arrive at an estimated pulse area representing the amount of light scattered by the particle and hence yielding a representation of the mass for that pulse. These pulse masses would be summed for the sample and reported along with the traditional channel counts.

The pulse-processing front-end 203 would be connected to an instrument controller 205, which would manage traditional functions like displaying information on a display 208. The display 208, in accordance with various aspects of the invention, is an LCD with touchscreen. The display 208, in accordance with various aspects of the invention, is a single LED indicating that particle counts are above some predetermined or configurable threshold. The scope of the invention is not limited by the type of display. The instrument controller 205 would also allow for the information to be logged to memory 207, either volatile or non-volatile or both, and would also allow for communication, through a communication module or unit 206, with external systems.

Sleep Between Samples

In accordance with the various aspects of the invention, the particle counters implement a concept referred to as locations and recipes, or some variant thereof. These allow users to collect air (or liquid) samples according to some pre-arranged parameters and schedule. For example, a unit might sample differently in different locations (more or less time) depending on these pre-configured requirements. In some cases an instrument might be placed, left, or unattended for an extended period of time and setup to perform periodic sampling for later retrieval or analysis (or for remote analysis).

If there is local power (plug-in or some similar outlet for power supply) then having the unit remain continuously power up (or on) is typically not an issue. In the case where the power source is a battery (limited supply of power) or it is a battery operated unit or instrumentation, this would limit the potential duration that such an instrument could remain continuously power up to operate, unattended. In accordance with various aspects of the invention, a second controller is added to such the unit or instrument to manage the power and shut the instrument down between samples, when the delay between such sampling is sufficiently long. The power control, through using a sleep or shut down mode, would greatly extended the amount of time such an instrument could operate, unattended or independent of the local power source.

The second controller could also provide a persistent memory to store the present state of the instrument between power cycles, and time keeping so it could wake-up after the desired delay so the next sample could be taken. The second controller would communicate the stored instrument state so the sampling could continue where it was before the instrument went to sleep or power cycled.

In accordance with some aspects of the invention, both controller can be implemented on a single controller. In accordance with some aspects of the invention, a second controller can be added that is a dedicated to power management. Hence, a lower-power controller can be used and power to most of the instrument's (or unit's) board can be shut off during these deep sleep periods, greatly increasing the life of the battery, which is an on-board battery.

Figure 3:
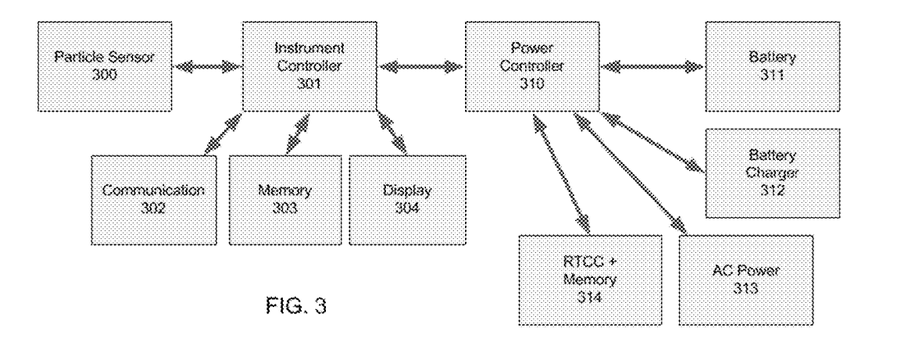
FIG. 3 is a particle counting system in accordance with the various aspects of the invention.

Referring now to FIG. 3, in accordance with aspects of the invention and another embodiment, a system is shown that includes two controllers configured. An instrument controller 301 controls the normal operation of the system or the particle counter, managing the particle sensor 300, which includes in this example all the pulse processing circuitry required to process pulses from particulates. The instrument controller 301 manages traditional functions like displaying information on some type of display 304, which might be as sophisticated as an LCD with touchscreen or as simple as a single LED indicating that particle counts are above some predetermined or configurable threshold.

The instrument controller 301 would also allow for the information to be logged to memory 303, which is either volatile memory or non-volatile memory or both, and would also allow for communication using, a communication module or unit 302, with external systems. In addition the instrument controller 301 would also communicate with a power controller 310 to ascertain the current power status of the system, for example the status of a battery 311, a battery charger 312, or whether AC power 313 is present, as well as possibly recovering non-volatile information like a current real-time-clock-calendar (RTCC) 314 values or some other stored parameters.

In between samples the Instrument controller 301 could request that the Power controller 310 shutdown power to the instrument circuits for example 300, 301, 302, 303, 304, and itself enter a low-power mode maintaining only the systems necessary for some period of time, that period perhaps a parameter supplied by the instrument controller 301 during the sleep request. The Power controller 310 would then comply shutting down power to most of the instrument for some predefined time (or until some other event occurs, for example a button press, insertion of AC power, etc.

Annotations in Recorded Data

Particle counters provide a mechanism to store sample data to a local memory area. This data can be accessed locally or downloaded to some remote system for more detailed analysis or processing. This data typically comprises information like the sample date/time, the channel counts for that sample, the location/recipe information for that sample and perhaps some environmental information or error/alarm conditions for the sample.

It is often difficult to remember conditions that were perhaps notable at the time of the sample, but otherwise go unrecorded in the data. In accordance with aspects of the invention, annotations are added to the data either before the fact, during the sample, or after the fact based on analysis or discussions with technicians or users.

In accordance with aspects of the invention, a text field is added to the recorded data samples (or as separate records in the log memory) and users can annotate the data using the text field. These annotations could be consulted at some later point when looking at the data and would provide context for the logged data. For example, in the case of high counts, for a particular sample, an annotation for that sample might record the fact that a door to a clean air was opened inadvertently by someone, or that a defective filter was located, or any number such events. In accordance with aspects of the invention, these notes could also be made either before the sample, during the sample or based on discussions or post-mortem after the data was recorded.

In accordance with aspects of the invention, the annotations could also be used to store particular tags in the data that could later be used to automate the preparation of particular reports. Automated report generators could process the data looking for these tags and perform certain actions based on these tags. For example, adding an annotation of <Rm101> to a number of samples could collect all the data from that annotation until another was encountered and report all this data as separate samples in a particular report. This could greatly simplify what is largely a manual process for many air quality consultants in aggregating sampling data into reports for clients.

Remote Access/Control (Concurrent Users)

In accordance with aspects of the invention, particle counters are devices that have one main microcontroller in charge of collecting particulate information, converting the particle counts into various formats, logging data, displaying information and communicating with external devices. For most instruments this consumes the bulk the controller's resources and often this means that overall system responsiveness is impacted when significant bandwidth is allocated to several of these tasks concurrently.

Implementing a particle counting instrument as a distributed system with multiple controllers sharing the load provides a means of partitioning the workload in such a way as to improve responsiveness of each section of the instrument. It allows the instrument to dedicate resources to the processing of particulate data, so that this task can occur unimpeded and reliably (which minimizes the chance of particulate information being lost due to interrupt latencies and such). Likewise a dedicated controller managing the user interface and manipulation of the data means that the user-interface remains responsive and that enhanced graphical display can be implemented. Finally, with a controller dedicated to external interfaces the system can ensure that such interfaces remain responsive during even high pulse throughput events.

In accordance with aspects of the invention, a distributed system also offers means of having multiple concurrent users. For example, a local user might be sampling data, and manipulating the graphical display interface to analyze the incoming data while the data is being sent automatically to a facility monitoring system, and one or more users access the data via web-browsers remotely. With this architecture a large number of such interfaces are possible concurrently.

In accordance with aspects of the invention, remote control of the instrument is possible. In a variety of situations it is desirable to be able to monitor the instrument remotely and control or configure it remotely. Rich external interfaces might allow for users to do such, either by controlling the local display and instrument directly (in the case where a supervisor might walk a subordinate through setting up an instrument for a particular task via a remote browser interface, so that the subordinate can monitor the changes as they occur). Or, the instrument could be controlled by the operator from a remote location, in the case of a unit mounted in a fixed location, or left in place to provide periodic monitoring.

In accordance with aspects of the invention, the remote access feature can also be used to upgrade instruments or units in the field with new configurations or features, without having to open the instrument to access the unit's internals.

User-Configurable Instrumentation

Most particle counters are instruments that are configured at the factory and retain that configuration over their lifetime. A few such instruments allow limited upgrades, but these are largely done as a fixed upgrade that would apply to an entire family or class of products and not to a particular instrument.

In accordance with aspects of the invention, significant advantages accrue if the individual instruments are upgradable in the field. This allows a manufacturer to offer maintenance subscriptions and upgrade paths for existing instruments, allowing such to be upgraded in-the-field without any removing the instrument from service, or downtime. In much the same way as computers and phones are now routinely upgraded, these instruments could upgrade themselves as bug fixes or new releases to the firmware became available.

In accordance with aspects of the invention, the upgrade might be initiated by the user rather than automated procedures, so that the user could choose whether or not to accept such an upgrade. It also allows an instrument to be purchased with one set of options and features and later upgraded to add additional options or features. For example, a 3 channel instrument with basic graphics and data analysis, could at some later date be upgraded to a 6 channel instrument with an advanced graphics package, and external facility monitoring interface. This could be done without adding any hardware or returning the unit to the factory.

In accordance with aspects of the invention, in one embodiment the user would access the manufacturer's website, and on selecting their instrument from a list of registered instruments adjust the feature set or options installed for that instrument purchase the desired upgrades and download them to a local computer from which they'd be installed directly to the instrument in question. In accordance with aspects of the invention, in another embodiment this all could be accomplished directly from the instrument in question. This capability allows a user to purchase a basic instrument and then to upgrade that instrument as their needs evolved over time, without being required to purchase an entirely new instrument.

Intelligent Sub-Systems

Typically particle counters have reasonably simple sub-systems. These include photo-amplifiers, laser controllers, pumps, batteries. Typically none of these have any local intelligence (as in microcontrollers or even memory) and only simple interfaces to the main system. This makes identification of individual components impossible (a counter cannot easily determine if a photo-amplifier, or pump has been changed from one use to the next). It also complicates troubleshooting instrument failures or predicting such ahead of time.

In accordance with aspects of the invention, adding local intelligence on sub-systems within the counter, the instrument or unit can provide enhanced functionality, reliability and diagnostics. For example each sub-system could contain model information with detailed operating parameters for that sub-system, as well as serial number information for the sub-system in question. This allows an instrument to ensure that the sub-systems in an instrument are the same sub-systems as were used during the last calibration (or alert the user to any changes). For some applications like the pharmaceutical industry such information is important as it would eliminate being able to use such an instrument for reporting.

It would also simplify the high-level particle counter implementation. In accordance with aspects of the invention, the module is allowed to manage the low-level operations. Thus, the instrument can simply provide high-level direction for the sub-system and leave the implementation of such to the sub-system itself. For example, the counter might request that the pump operate at 75.2% of its rated power and adjust this value up or down as required to achieve a desired flow, rather than having to attempt to control a motor to achieve this. This means that various pumps could be substituted in an instrument over its lifetime without the main counter firmware having to change to manage a large number of pumps. It also means that pumps with significantly different flow rates can be interfaced similarly, without significant changes to the instrument. In some instrument the flow rate might be 0.1 CFM, in others 1 CFM or even 10 CFM without requiring different interfaces even though the pumps themselves and their controllers are vastly different.

In accordance with aspects of the invention, having local control allows intelligence to be embedded in the sub-systems. That intelligence can provide real-time control and monitoring of components in the sub-system as well as providing statistical lifetime information, and performing predictive analysis. The real-time control we've already discussed, the lifetime statistical information allows a unit track the total hours its run, the minimum and maximum and average conditions it encountered during its lifetime. A log of any errors encountered over its lifetime, etc. Since it tracking lifetime performance, the system can provide warnings as control parameters approach end-of-life or failure conditions. For example, by tracking current of the pump over its life, the system could provide an early-warning indication of impending failure of such before it occurs. This would allow a user to plan preventive maintenance before such causes a removal of service for the instrument. Furthermore, by tracking operational parameters, the system might also be able to determine when an instrument should be recalibrated, using more than simply elapsed time.

The sub-system alerts are based on parameters within the sub-system itself. These could be adjusted remotely in order to adjust the response of these systems over time, and to refine their behavior as historical information for these accrues over the product life-cycle and algorithms refine these behaviors to render them more accurate and useful.

Advanced Alarming

Most particle counters have reasonably simplistic alarming. This normally consists of a simple alarm threshold for each channel. Once a channel reaches this threshold alarms are asserted. An extension of this adds alarming to specific recipes. In accordance with aspects of the invention, alarm thresholds for one sampling setup might differ from others. That makes sense since the conditions might well differ as well. In some cases the system is measuring the air in a relatively clean location and would want the alarms for that area to differ than sampling, the system might do in a significantly less clean location. Examples of these might be a gowning room in a cleanroom which is a relatively gray area compared to the highly regulated environment of the cleanroom proper. Many other such examples exist. This allows these alarms to be defined in this way, so that they take precedence of channel alarm thresholds, so that the user doesn't have to adjust the channel alarms in order to create different alarm thresholds for different "recipes" or location samples. Also, both traditional alarms and recipe alarms can also be configured with thresholds based on the particulate mass calculation rather than counts on a specific channel. This allows for capabilities that are not implemented on existing instruments.

In accordance with aspects of the invention, alarms can be specified for environmental conditions (as in temperature or relative humidity), which extends the capabilities of the instrument for monitoring and reacting to more than just particulates. As other intelligent sensors are added to the instrument (through an intelligent port) these can also be used for alarming. Such sensors include but are not limited to: air velocity, differential pressure, various gas sensors, etc.

Advanced Graphs/Charts

Particle counters typically display counts for a sample period as accumulating counts over the period in question, either the counts for a specific channel itself or the sum of counts for that channel and all the other larger channels. This information is usually displayed as raw count numbers and it can be difficult to determine trends in such data while simply looking at numbers increasing on a display. Displaying the delta in these counts over a short period (say 1 second) is an attempt to make variations in the data more evident. It's still difficult however to visualize either trending changes or periodic changes by looking at values.

Figure 4:
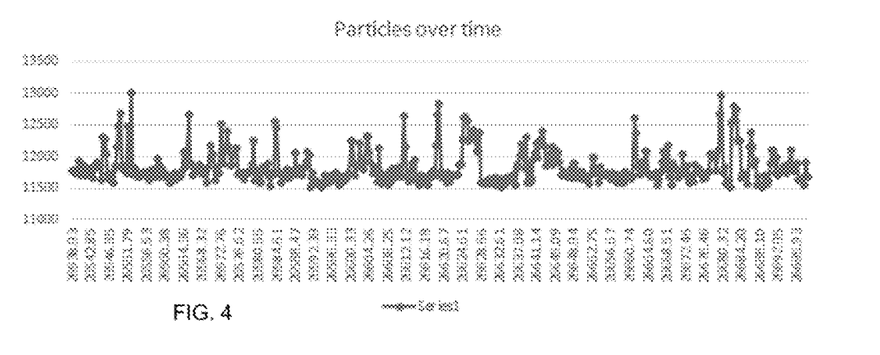
FIG. 4 is a graph illustrating counts over a period of time in accordance with the various aspects of the invention.

In accordance with aspects of the invention, graphs and charts are particularly useful for providing visual indications of such trends. Referring now to FIG. 4, a means of visualizing changes in particulates over time is illustrated, which shows graphing of instrument data. These can be run in real-time on data arriving into the instrument or they might also be run on data already logged within the instrument. The bottom axis is time, in seconds. The vertical axis is particle counts for a particular sample. In this case there is an average of ~12,000 particles/second and, the system can see the variations in this data. In accordance with the various aspects of the invention, an advanced instrument captures data much more quickly and could map this data with a much finer time resolution. That data could then be further analyzed with any number of techniques or graphs to provide more detailed information on the data. For example an FFET (Fast-Fourier-Transform) would provide a frequency analysis of the data and might pinpoint certain frequencies at which particulates are arriving at the instrument. These frequencies might provide indications as to possible sources for these particulates.

Figure 5:
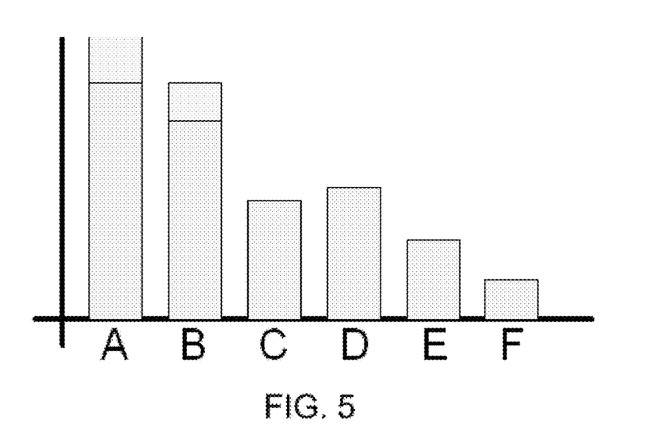
FIG. 5 is a graph illustration of the counts in accordance with the various aspects of the invention.

The instrument could graph from each channel simultaneously, or the instrument could provide a multi-channel histogram, as shown in FIG. 5, to display relative views of the data for each channel, perhaps with the alarm thresholds coded in a separate color for counts above some pre-defined alarm threshold.

Alternatively this "equalizer" type display could have horizontal bars with the maximums for each channel persistent for some short period (handful of seconds) that way as the bars changed the local maxima could be persistent to show local short-term trend information.

Real-Time Meter

Particle counters are typically used to monitor and record particle counts over time. It can be quite challenging to use them to attempt to discern the source of particulates. This is often largely because of the way the information is displayed (as cumulative counts, and as numbers on the screen which must be interpreted real-time to make decisions as to the likely direction of particulates as the counter is moved about). In accordance with the various aspects of the invention, beeping above some threshold, or alarming, to attempt to improve the responsiveness of these instruments to particulate sources.

Figure 6:
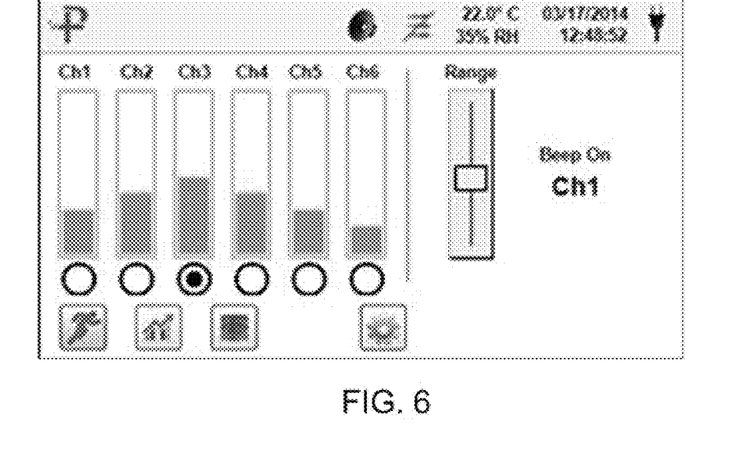
FIG. 6 is a display for presenting the data in real-time in accordance with the various aspects of the invention.

Referring now to FIG. 6, a display is shown, in accordance with the various aspects of the invention, for presenting the data in real-time in such a way as to be visually responsive to the present state of particles as they arrive into the instrument. This simplifies the tracking of such particles to their source. The display gives a visual indication of 6 channels of data. This particular histogram has a log scale that gives a relative indication of particulate traffic for each channel. The Range slider adjusts the sensitivity of the counters, so that the user can adjust it as the source of the particulates are approached so the system doesn't saturate the chart. The intention is that the user adjusts the slider to try and keep the maximum channel near the middle of the range. This provides strong visual feedback of the particulate data in real-time that can be used to facilitate tracking particulates to their source.

In addition to this display, the system can also provide similar functionality via audio, either through an on-board audio transducer or external headphone or earbud. The instrument could output either a set of pulses indicative of the scale (increasing frequency based on the height of the selected channel, or a tone with a frequency indicative of the height of the selected channel (with a low frequency tone indicating fewer particles and a higher tone indicating more particles). This would allow a user to use this instrument without having to continually look at the display (in cases where they are looking at potential particulate sources around equipment etc.).

In accordance with aspects of the invention, in order to provide a smoother audio output the rate of change for the audio signal can be limited, such that it provided a more continuous tone with a more slowly varying frequency despite what might be dramatically different variations in particulate rates.

In accordance with aspects of the invention, a number of different embodiments are possible for audio. The instrument or unit could be designed to have an output like a Geiger counter, with increasing pulse rate indicative of the particle volume encountered (at a particular sensitivity). It could also have an output like a metal detector with a tone of varying frequency (again based on the present sensitivity setting).

Pulse Log Buffer

Particle counters process pulses as they arrive. In accordance with aspects of the invention, particle counters measure the pulse height and sometimes the pulse width and then increment the counter for a particular channel based on one or both of these parameters. Once this is done detailed information on an individual pulse is discarded.

If this and other parameters, for each pulse, are stored in a pulse log buffer, it could be used to provide more detailed analysis on particulates. If the system stored the time of arrival for a pulse, the pulse height, and width, then the system could use this information to calculate a more accurate mass (as in item 1 above), though this might be done in real-time. But, having the data time-stamped would allow us to run more detailed temporal analyses on the data. A more accurate FFT might reveal patterns in the data, it might identify issues in the airflow (both external and internal to the counter, for example it might signal pulsations in the airflow caused by a failing pump).

When particle concentrations are large this might well constitute an enormous amount of data, arriving at a high data rate. Under such conditions the data needs to be cached quickly in a large memory. Present day FPGAs and SRAM, SDRAM, or DRAM memory chips are particularly suited to this task. A particular capture profile might also be provided (limiting the data captured based on time, particle size, particle area, or some snapshot after a trigger event (for example capture 'n' particles when before, during or after a particular particle density is reached).

Sophisticated triggers can limit the data captured and hence post-capture analysis to events that are particularly of interest or concern. The intention is to provide features commonly seen on a digital storage oscilloscope, as to triggering, capture, and display of the data. In addition to complex triggers, multiple events could be captured, averaged, or gleaned for minimum/maximum values to provide an envelope for the event. The data could be processed locally or downloaded to a local controller for further processing or display or exported to an external computer for further analysis or manipulation. This functionality also provides the means to potentially improve calibration of an instrument. If extensive data is captured or collected during the calibration process, the a more accurate individual channel criteria can be derived to arrive at better separation between adjacent channels, and therefore allow many more discriminated channels within an instrument.

Instrument Network

In accordance with aspects of the invention, particle counters can be individual instruments and networked. In accordance with aspects of the invention, some are networked and connected to facility monitoring systems or to central networks within a facility. At times instruments are networked locally and perhaps connected to external data collection or display units. In accordance with aspects of the invention, connecting a system with multiple particle counters through a simple hub/switch to a more sophisticated counter with a display allows for a very low-cost system that can be installed simply and provide display, logging and reporting from low-cost particle counters without each requiring a display or sophisticated interface. It does so without requiring computers or external monitors be installed and loaded with data collection and analysis firmware.

Figure 7:
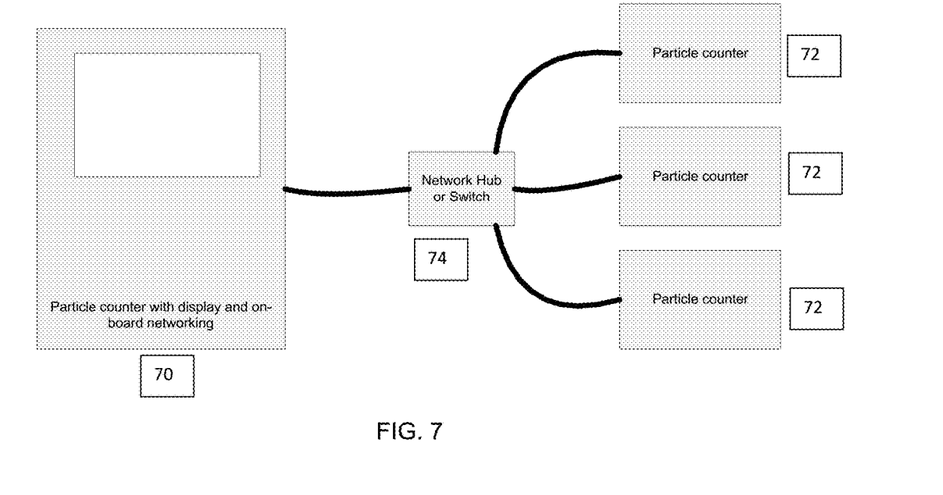
FIG. 7 is a particle counter system in accordance with the various aspects of the invention.

In accordance with aspects of the invention, referring to FIG. 7, in one embodiment is shown with a particle counting instrument 70 is shown with particle counters 72 (each, in accordance one aspect of the invention, without a display) and an Ethernet network hub or switch 74. In accordance with aspects of the invention, the instruments/particle counters/units communicate via a number of means, some of which include WiFi, RS-485, RS-232, Zigbee, Bluetooth, or any number of other links. Thus, a small network can easily be formed without requiring external hardware and software. This significantly lowers the cost and complexity of setting up a small monitoring system in an area. Such a system could be used to implement a small monitoring system for a manufacture that has only a small clean area, perhaps in final assembly or the like.

In accordance with aspects of the invention, it also provides a means of deploying such a system for troubleshooting in a large factory. For example in a large pharmaceutical factory, or when qualifying a new process line in a manufacturing plant, a simple system could be setup like the above with dozens of low-cost particle counters and one larger unit with a display. The larger unit could be setup to acquire data from each of the smaller counters and to display that data either in series (cycling through the counters one at a time), or by using tiles or a scrollable window to allow data from all of the counters to be summarized or displayed. The main counter could also preferentially display data from the counters, for example in the case of alarms on a particular sensor its data could rise to the top of a list or appear instead of or on top of other normal data.

Adding an external vacuum pump, some vacuum hose and power supply would make the system reasonably self-contained. It could be mounted on a cart for rapid deployment in the case of an event detected in a factory allowing for quick analysis of a problem, in the hopes of speedy resolution. In many of these installations downtime is very costly, so a system that can be rapidly deployed and provide quick and effective monitoring of dozens or more nodes is of value.

Though not shown, the external counters could be a variety of different types of counters, of classes of counters with varying functionality, sensitivity, or number of channels from a single manufacturer or from many manufacturers. The main counter would know how to interface to each of these and how to display the data particular to any one counter (which also providing summary data common to all counters, as in number of counts for each installed channel, and the size of each channel).

It will be apparent that various aspects of the invention as related to certain embodiments may be implemented in software, hardware, application logic, or a combination of software, hardware, and application logic. The software, application logic and/or hardware may reside on a server, an electronic device, or be a service. If desired, part of the software, application logic and/or hardware may reside on an electronic device and part of the software, application logic and/or hardware may reside on a remote location, such as server.

In accordance with the teaching of the invention and certain embodiments, a program or code may be noted as running on a computing device, instrument, or unit. The computing device is an article of manufacture. Examples of an article of manufacture include: an instrument, a unit, a server, a mainframe computer, a mobile telephone, a multimedia-enabled smartphone, a tablet computer, a personal digital assistant, a personal computer, a laptop, or other special purpose computer each having one or more processors (e.g., a controller, a Central Processing Unit (CPU), a Graphical Processing Unit (GPU), or a microprocessor) that is configured to execute a computer readable program code (e.g., an algorithm, hardware, firmware, and/or software) to receive data, transmit data, store data, or perform methods. The article of manufacture (e.g., computing device) includes memory that can be volatile or non-volatile. The memory, according to one aspect, is a non-transitory computer readable medium having a series of instructions, such as computer readable program steps encoded therein.

In accordance with aspects and certain embodiments of the invention, the non-transitory computer readable medium includes one or more data repositories. The non-transitory computer readable medium includes corresponding computer readable program code and may include one or more data repositories. Processors access the computer readable program code encoded on the corresponding non-transitory computer readable mediums and execute one or more corresponding instructions.

Other hardware and software components and structures are also contemplated. Unless defined otherwise, all technical and scientific terms used herein have the same meaning as commonly understood by one of ordinary skill in the art to which this invention belongs. Although any methods and materials similar or equivalent to those described herein can also be used in the practice or testing of the invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or system in connection with which the publications are cited. The citation of any publication is for its disclosure prior to the filing date and should not be construed as an admission that the invention is not entitled to antedate such publication by virtue of prior invention. Further, the dates of publication provided may be different from the actual publication dates which may need to be independently confirmed.

All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the invention, therefore, is not intended to be limited to the exemplary embodiments shown and described herein. Rather, the scope and spirit of invention is embodied by the appended claims.

The invention claimed is:

1. A particle counting system comprising:
at least one particle sensor including at least one output channel generating an electrical signal for a particle passing through the sensor,
where the electrical signal for the output channel includes at least a peak pulse height,
where the peak pulse height is converted to a digital value based on previous calibration values to infer relative particulate size for the peak pulse height,
where a plurality of peak pulse heights, that include the peak pulse height, are summed for a period of time to determine a summed value,
where a density and at least one of a configurable and a fixed refractive index is applied to the summed value to infer total particle mass for the period, and
where the summed value indicates a total particle mass for the period and is a more accurate particle mass for the period than an average mass calculated by multiplying a particle count by an average size for the output channel.

2. The system in claim 1, wherein the output channel generates an electrical signal representing a pulse width of the particle pulses, where both the peak pulse height and the pulse width are multiplied to provide an estimate of an area of scattered light, and where the area is used in the total particle mass sum.

3. The system in claim 2, where the area is calculated by fitting a characteristic curve for pulses from the peak pulse height and the pulse width to yield a more accurate area of scattered light.

4. The system in claim 1 further comprising:
a battery; and
a controller in communication with the battery and the at least one particle sensor, the controller manages power by monitoring at least one of: AC power, voltage levels, the battery's charging and the battery's discharging.

5. The system in claim 4 further comprising a display in communication with the controller, where information from the controller can be displayed.

* * * * *